(12) United States Patent
Mertens et al.

(10) Patent No.: US 6,740,720 B2
(45) Date of Patent: May 25, 2004

(54) WATER-SOLUBLE HOMOPOLYMERS AND COPOLYMERS HAVING AN IMPROVED ENVIRONMENTAL ACCEPTABILITY

(75) Inventors: Richard Mertens, Krefeld (DE); Gregor Herth, Krefeld (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 10/344,694

(22) PCT Filed: Jun. 1, 2001

(86) PCT No.: PCT/EP01/06236

§ 371 (c)(1), (2), (4) Date: Feb. 24, 2003

(87) PCT Pub. No.: WO02/16445

PCT Pub. Date: Feb. 28, 2002

(65) Prior Publication Data

US 2003/0181620 A1 Sep. 25, 2003

(30) Foreign Application Priority Data

Aug. 23, 2000 (DE) .......................................... 100 41 392

(51) Int. Cl.⁷ ............................................... C08F 226/02
(52) U.S. Cl. ................... 526/307.6; 526/220; 526/236; 526/303.1; 526/317.1; 526/318.5
(58) Field of Search ................. 526/220, 236, 526/303.1, 307.6, 317.1, 318.5

(56) References Cited

U.S. PATENT DOCUMENTS

| | | | |
|---|---|---|---|
| 3,780,006 A | 12/1973 | Zweigle | |
| 4,929,717 A | * 5/1990 | Chmelir | ...................... 528/490 |
| 5,229,466 A | 7/1993 | Brehm et al. | |

FOREIGN PATENT DOCUMENTS

| | | |
|---|---|---|
| DE | 1 041 248 | 10/1958 |
| DE | 1 070 377 | 12/1959 |
| DE | 35 39 385 | 5/1986 |
| DE | 35 44 770 | 6/1988 |
| DE | 31 35 149 | 5/1991 |
| DE | 40 34 642 | 5/1992 |
| DE | 3432690 | 9/1993 |
| DE | 197 52 127 | 7/1999 |
| DE | 197 52 128 | 7/1999 |
| DE | 196 36 494 | 11/2000 |
| EP | 0 505 163 | 9/1992 |
| FR | 1 549 213 | 12/1968 |
| JP | 56-103207 | 8/1981 |
| JP | 07-305002 | * 11/1995 |
| SU | 1994-032738 | 12/1992 |
| WO | 99 26988 | 6/1999 |

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

The invention relates to water-soluble homopolymers and copolymers, which comprise an EbC50 value according to the algae toxicity test of *Scenedesmus subspicatus* of grater than 10 mg/l. The invention also relates to the production and use of these polymers as flocculation aids or thickeners and as a constituent of a plant protective agent or of an erosion protective agent.

33 Claims, No Drawings ated monomer content without affecting the solubility of the corresponding polymers, said disclosure describes a process in which at least 1% by weight of sulphites, bisulphites or pyrosulphites is added to the acrylamide-containing polymers, which are then dried at 50 to 100° C.

WATER-SOLUBLE HOMOPOLYMERS AND COPOLYMERS HAVING AN IMPROVED ENVIRONMENTAL ACCEPTABILITY

BACKGROUND OF THE INVENTION

1. Field of the Invention

The present invention relates to water-soluble homopolymers and copolymers having an $E_bC_{50}$ value of more than 10 mg/l in the algae toxicity test on *Scenedesmus subspicatus*. The present invention further relates to the preparation of these polymers and to their use as flocculation aids or thickeners and as constituents of plant protection agents or erosion protection agents.

2. Description of the Background

Water-soluble homopolymers and copolymers are currently widely used inter alia as constituents of plant protection or erosion protection agents. As these polymers are frequently used in the open countryside, their toxicological properties are becoming increasingly important. In particular, polymers based on acrylic acid, methacrylic acid or their derivatives have a toxic effect on humans and other mammals, as well as on microorganisms such as algae. Because of their toxic effect on microorganisms, the use of these polymers in the open countryside, for example in soils, is not completely harmless, so there has been no lack of attempts in the past to develop polymers with a smaller toxic effect.

In a number of known processes, the residual monomer content is reduced by aftertreating the polymers with amines. Thus DE-AS 1 041 248 describes a process for reducing the residual content of monomeric acrylamide in acrylamide-containing water-soluble copolymers by treating the polymers with ammonia or a primary or secondary amine. The residual content of monomeric acrylamide can be reduced to approx. 0.1% by weight using this process. The copolymers obtainable in this way are said to have a lower toxicity to rats and cats than the untreated polymers.

DE 35 39 385 A1 discloses a process for the production of polymer gel particles in which the polymer gel is fed through a special roller device. To reduce the content of acrylamide monomer in acrylamide-containing homopolymers and copolymers, alkaline compounds, substances containing active hydrogen or compounds capable of forming active hydrogen are added to the cutting mechanism of this roller device. Examples of such compounds are alkali metal and alkaline earth metal hydroxides, sulphites and amines, inter alia.

To reduce the residual acrylamide monomers, DE 197 52 127 and DE 197 52 128 teach the addition of ammonia and amines or ammonium salts to the monomer solution before polymerization. To achieve the desired effect, the products have to be dried at more than 120° C. Crosslinking reactions occur at these high temperatures and lead to a marked decrease in the solubility of the polymers. This applies especially to copolymers which, in addition to acrylamide, also contain ionic comonomers such as sodium acrylate.

Such partial insolubilities due to the aftertreatment, whether it be because of the chosen aftertreatment reagents or because of the high aftertreatment temperature, are described in JP 56-103207 using copolymers of sodium acrylate and acrylamide as an example. According to said disclosure, aftertreatment of the appropriate polymers with 1% by weight of ammonia, amines or thiosulphates, based in each case on the polymer, followed by drying at a temperature of 150° C., leads to insolubility of almost all the polymer. Aftertreatment with ammonia or an amine leads to partial insolubility of the polymers, even at a low drying temperature of 50° C. To reduce the residual monomer A similar process for the preparation of acrylamide-containing copolymers is described in DE 1 070 377. In this process the polymer is aftertreated with an aqueous solution of sodium bisulphite or sodium metabisulphite, the sulphites being used in amounts of at least 1 mol of sulphite per mol of residual acrylamide. A reduction in the residual monomer content to about 0.01% is achieved using this process.

U.S. Pat. No. 3,780,006 discloses the use of gaseous sulphur dioxide for the same purpose.

EP 0 505 163 A1 describes a process in which superabsorbent polymers are treated with surface-active compounds and substances capable of reacting with a vinyl double bond, for example sulphites, bisulphites, sulphinic acids, cysteine or lysine. The residual monomer content of (meth)acrylic acid can be reduced to less than 10 ppm by this process. However, the process gives rise to a comparatively high degree of secondary crosslinking in the case of non-crosslinked polymers.

Many of the processes known in the state of the art for reducing the residual monomer content have the disadvantage that the substances used to aftertreat the polymers, optionally in combination with the temperatures applied during the aftertreatment, impair the solubility or other engineering properties of the polymers. Moreover, the majority of known processes are restricted to acrylamide-containing polymers. Furthermore, insufficient attention has been paid to the aspect of the toxicity of the known polymers to microorganisms. However, a sufficiently low toxicity of the polymers to microorganisms, for example algae, is particularly desirable from the ecological point of view for their use in the open countryside.

SUMMARY OF THE INVENTION

The object of the present invention is therefore to provide water-soluble polymers which, compared with polymers of the state of the art, have an improved environmental compatibility coupled with otherwise at least equivalent product properties, especially at least the same water solubility.

The object is achieved according to the invention by the provision of water-soluble polymer particles having an $E_bC_{50}$ value of more than 10 mg/l in the algae toxicity test on *Scenedesmus subspicatus*.

DETAILED DESCRIPTION OF THE PREFERRED EMBODIMENTS

The present invention relates to both homopolymer and copolymer particles. The monomers used are preferably acrylic acid and methacrylic acid, acrylic acid derivatives such as salts of acrylic acid and methacrylic acid, acrylamide, methacrylamide, acrylonitrile, methacrylonitrile, N,N-dimethylacrylamide, vinyl-pyridine, vinyl acetate, water-soluble, ethylenically unsaturated organic acids such as maleic acid, fumaric acid, itaconic acid, vinylsulphonic acid and acrylamido-methylpropanesulphonic acid, and salts thereof, hydroxyl group-containing esters of polymerizable acids, such as hydroxyethyl and hydroxypropyl esters of acrylic acid and methacrylic acid, and amino group-containing esters of polymerizable acids, such as dimethylaminoalkyl and diethylaminoalkyl esters and amides of acrylic acid and methacrylic acid. It is also possible to modify the copolymers by using monomers containing sulpho groups and sulphate groups, such as (meth)allylsulphonic acid, vinylsulphonic acid, styrenesulphonic acid and acrylamidomethylpropanesulphonic acid, monomers containing phospho groups, such as vinylphosphonic acid, allylphosphoric acid, acrylamidomethylpropanephosphonic acid and salts thereof, hydroxyethyl (meth)acrylate sulphates, allyl alcohol sulphates and phosphates, polyalkylene glycol esters of (meth) acrylic acid and polyalkylene glycol ethers with (meth)allyl alcohol. If an acid is used as the monomer, this can be in the form of the free acid, neutralized or partially neutralized. The neutralization or partial neutralization can be carried out with any base or any mixture of suitable bases that form a water-soluble salt with the acid, especially alkali metal hydroxides, alkaline earth metal hydroxides and/or ammonia.

The polymer particles preferably contain at least one acrylic acid derivative/methacrylic acid derivative or acrylic acid/methacrylic acid as the monomer.

Particularly preferably, the polymer particles additionally contain at least one other polymerized monomer from the group comprising monoethylenically unsaturated $C_{3-10}$ monocarboxylic acids and their alkali metal, ammonium and amine salts, and at least one other polymerized monomer suitable for modifying the copolymers.

Very particularly preferably, the water-soluble polymer particles according to the invention consist of 1 to 99% by weight of acrylamide and 99 to 1% by weight of acrylic acid neutralized to the extent of 0 to 100 mol %.

Surprisingly, water-soluble polymer particles with an $E_bC_{50}$ value of more than 10 mg/l in the algae toxicity test on *Scenedesmus subspicatus* can be obtained by heat-treating the polymer particles and adding at least one ammonium salt and one water-soluble amine to the monomer solution before polymerization or to the polymer after polymerization, but before the heat treatment.

According to the invention, the ammonium salts used are water-soluble inorganic and organic salts of ammonia.

The inorganic ammonium salts used are preferably the fluorides, chlorides, bromides, iodides, sulphates, sulphites, sulphoxylates, phosphates, phosphonates, nitrates and nitrites of ammonia.

Suitable organic ammonium salts are salts of aliphatic and aromatic acids and salts of acids containing both aliphatic and aromatic groups. It is preferable to use salts of formic acid, acetic acid, propionic acid, butyric acid, lactic acid, oxalic acid, maleic acid, fumaric acid, glutaric acid, methanesulphonic acid, aspartic acid, benzoic acid, toluenesulphonic acid, styrenesulphonic acid, naphthalenesulphonic acid or benzene-sulphonic acid.

The amount of ammonium salt used is preferably 0.05 to 10% by weight and particularly preferably 0.2 to 3% by weight, based on the product.

The amine components used can be any water-soluble amines or a mixture of at least two amines, such as aliphatic monoamines and polyamines, cycloaliphatic mono-amines and polyamines, heterocyclic amines and alkanolamines. It is preferable to use aliphatic $C_1$–$C_{10}$ amines, cycloaliphatic $C_1$–$C_{10}$ amines and aromatic $C_6$–$C_{12}$ amines. It is particularly preferable to use alkanolamines and very particularly preferable to use isopropanolamine.

The amount of water-soluble amine used is preferably 0.1 to 12% by weight and particularly preferably 0.5 to 5% by weight, based on the product.

The ammonium salt or mixture of at least two ammonium salts and the amine or mixture of at least two amines can be added in any process step before the polymer is heat-treated. The components do not have to be added at the same stage of the process. Thus, for example, it is possible to add the ammonium salt to the reaction solution before polymerization and the amine component immediately before the heat treatment. The individual components can each be added in one process step or in portions over different process steps. For example, it is possible to add part of an ammonium salt to the monomer solution before polymerization and the remainder of the ammonium salt to the polymer immediately before the heat treatment. Preferably, however, the ammonium salt or mixture of at least two ammonium salts and the amine or mixture of at least two amines are added to the process in the same step, either to the monomer solution before polymerization or to the polymer after comminution and immediately before the heat treatment.

The polymers, in the form of a gel after polymerization, are comminuted as a preparation for the heat treatment.

At least one ammonium salt and at least one amine must be added to the polymer at the latest before the heat treatment begins. The heat treatment is carried out at a temperature of 80 to 120° C. and preferably of between 90 and 110° C.

Finally, the dried polymers are comminuted again, ground and separated into the required sieve fractions.

Compared with the polymers known in the state of the art, the polymer particles according to the invention are distinguished by their improved environmental compatibility based on their low toxicity, especially to microorganisms such as algae. Toxicity to algae can be measured using $E_bC_{50}$ values. The $E_bC_{50}$ value indicates the test substance concentration at which the growth of an algae culture previously in the exponential growth phase is inhibited by 50%. Whereas the polymers of the state of the art essentially have $E_bC_{50}$ values of <10 mg/l, the polymer particles according to the invention of the same composition always have significantly higher $E_bC_{50}$ values of >10 mg/l. Because of their low toxic potential, the polymer particles according to the invention are to be used in preference to the polymers known in the state of the art from the ecological point of view, especially in the open countryside. The other product properties of the polymer particles according to the invention, especially their water solubility, are at least equivalent to those of the polymers known hitherto for this purpose. As their preparation does not involve any other additives capable of causing secondary reactions, the product properties of the polymer particles according to the invention are normally even superior to those of the polymers of the state of the art.

The present invention further relates to a process for the preparation of the water-soluble polymer particles according to the invention by polymerizing a monomer solution, heat-treating the resulting polymer particles and adding at least one ammonium salt and one water-soluble amine to the monomer solution before polymerization or to the polymer after polymerization, but before the heat treatment.

The present invention relates to the preparation of both homopolymer and copolymer particles. The monomers used are preferably acrylic acid and methacrylic acid, acrylic acid derivatives such as salts of acrylic acid and methacrylic acid, acrylamide, methacrylamide, acrylonitrile, methacrylonitrile, N,N-dimethylacrylamide, vinyl-pyridine, vinyl acetate, water-soluble, ethylenically unsaturated organic acids such as maleic acid, fumaric acid, itaconic acid, vinylsulphonic acid and acrylamidomethylpropanesulphonic acid, and salts thereof, hydroxyl group-containing esters of polymerizable acids, such as hydroxyethyl and hydroxypropyl esters of acrylic acid and methacrylic acid, and amino group-containing esters of polymerizable acids, such as dimethylaminoalkyl and diethylaminoalkyl esters and amides of acrylic acid and methacrylic acid. It is also possible to modify the copolymers by using monomers containing sulpho groups and sulphate groups, such as (meth)allylsulphonic acid, vinylsulphonic acid, styrenesulphonic acid and acrylamidomethylpropanesulphonic acid, monomers containing phospho groups, such as vinylphosphonic acid, allylphosphoric acid, acrylamidomethylpropanephosphonic acid and salts thereof, hydroxyethyl (meth)acrylate sulphates, allyl alcohol sulphates and phosphates, polyalkylene glycol esters of (meth) acrylic acid and polyalkylene glycol ethers with (meth)allyl alcohol. If an acid is used as the monomer, this can be in the form of the free acid, neutralized or partially neutralized. The neutralization or partial neutralization can be carried out with any base or any mixture of suitable bases that form a water-soluble salt with the acid, especially alkali metal hydroxides, alkaline earth metal hydroxides and/or ammonia.

The monomer used is preferably at least one acrylic acid derivative/methacrylic acid derivative or acrylic acid/methacrylic acid.

It is particularly preferable additionally to use at least one other monomer from the group comprising monoethylenically unsaturated $C_{3-10}$ monocarboxylic acids and their alkali metal, ammonium and amine salts, and/or at least one other monomer suitable for modifying the copolymers.

Very particularly preferably, the monomer solution used contains as monomers 1 to 99% by weight of acrylamide, based on the total amount of monomers, and 99 to 1% by weight of acrylic acid neutralized to the extent of 0 to 100 mol %.

At least one ammonium salt or at least one amine, or a mixture of at least one ammonium salt or a mixture of at least one amine, is optionally added to the monomer solution, which preferably contains 15 to 50% by weight of monomers.

The polymerization reaction is initiated by adding the polymerization initiators known to those skilled in the art, such as peroxide compounds, peroxide sulphates, azo compounds, redox systems and photoinitiators. Initiation is preferably effected using a redox system, composed of an oxidizing agent and a reducing agent, or a photoinitiator.

The oxidizing agents are used in a concentration of 0.00005 to 0.5% by weight and preferably of 0.001 to 0.1% by weight, based in each case on the polymerization solution. The oxidizing agents preferably used are peroxide compounds such as alkali metal or ammonium persulphates, alkali metal or ammonium perphosphates, hydrogen peroxide or its salts, benzoyl peroxide, butyl hydroperoxide or peracids, although it is also possible to use other oxidizing agents such as, preferably, potassium permanganate, sodium or potassium chlorate or potassium dichromate.

The reducing agents are also used in a concentration of 0.00005 to 0.5% by weight and preferably of 0.001 to 0.1% by weight, based in each case on the monomer solution. The reducing agents preferably used are sulphur-containing compounds such as sulphites, thiosulphates, sulphinic acid or organic thiols, low-valency metal salts such as copper(I), manganese(II) or iron(II) salts, ascorbic acid, or phosphorus compounds such as sodium hypophosphite.

In the case of a photopolymerization, the reaction is started with UV light to decompose the initiator. The initiators used are preferably benzoin and benzoin derivatives such as benzoin ethers, benzil and its derivatives such as benzil ketals, acrylodiazonium salts, azo initiators, e.g. 2,2'-azobis(isobutyronitrile) or 2,2'-azobis-(2-amidinopropane) hydrochloride, or acetophenone derivatives. 0.001 to 0.1% by weight and preferably 0.002 to 0.05% by weight is used for the photoinitiation.

The polymerization is carried out in aqueous solution, either batchwise in a polymerization vessel or continuously on an endless belt, for example as described in DE 35 44 770. Said document is introduced herewith as a reference and forms part of the disclosure. The process is started at a temperature of between −20 and 50° C., preferably of between −10 and 10° C., and at atmospheric pressure without an external heat supply, the heat of polymerization raising the temperature to a maximum final value of 50 to 150° C., depending on the content of polymerizable substance.

When the polymerization is complete, the polymer, in the form of a gel, is comminuted.

At the latest after this process step, at least one ammonium salt and at least one amine are added to the polymer, provided none of these components has been added in a previous process step, and the remainder of at least one amine and/or at least one ammonium salt is added, provided these components have not been added in their entirety in a previous process step.

According to the invention, the ammonium salt or mixture of at least two ammonium salts and the amine or mixture of at least two amines can be added in any process step before the polymer is heat-treated. The components do not have to be added at the same stage of the process. Thus, for example, it is possible to add the ammonium salt to the reaction solution before polymerization and the amine component immediately before the heat treatment, or the amine is added to the monomer solution and the ammonium salt to the polymer gel. The individual components can each be added in one process step or in portions over different process steps. For example, it is possible to add part of an ammonium salt to the monomer solution before polymerization and the remainder of the ammonium salt to the polymer immediately before the heat treatment. Preferably, however, the ammonium salt or mixture of at least two ammonium salts and the amine or mixture of at least two amines are added to the process in the same step, either to the monomer solution before polymerization or to the polymer after comminution and immediately before the heat treatment.

The ammonium salts used according to the invention are water-soluble inorganic and organic salts of ammonia.

The inorganic ammonium salts used are preferably the fluorides, chlorides, bromides, iodides, sulphates, sulphites, sulphoxylates, phosphates, phosphonates, nitrates and nitrites of ammonia.

Suitable organic ammonium salts are salts of aliphatic and aromatic acids and salts of acids containing both aliphatic and aromatic groups. It is preferable to use salts of formic acid, acetic acid, propionic acid, butyric acid, lactic acid, oxalic acid, maleic acid, fumaric acid, glutaric acid, methanesulphonic acid, aspartic acid, benzoic acid, toluenesulphonic acid, styrenesulphonic acid, naphthalenesulphonic acid or benzene-sulphonic acid.

The amount of ammonium salt used is preferably 0.05 to 10% by weight and particularly preferably 0.2 to 3% by weight, based on the product.

The amine components used can be any water-soluble amines or a mixture of at least two amines, such as aliphatic monoamines and polyamines, cycloaliphatic mono-amines and polyamines, heterocyclic amines and alkanolamines. It is preferable to use aliphatic $C_1$–$C_{10}$ amines, cycloaliphatic $C_1$–$C_{10}$ amines and aromatic $C_6$–$C_{12}$ amines. It is particularly preferable to use alkanolamines and very particularly preferable to use isopropanolamine.

The amount of water-soluble amine used is preferably 0.1 to 12% by weight and particularly preferably 0.5 to 5% by weight, based on the product.

The comminuted polymer is then heat-treated at a temperature of 80 to 120° C. and preferably at 90 to 110° C.

Finally, the dried polymers are comminuted again, ground and separated into the required sieve fractions.

The process according to the invention makes it possible to prepare polymer particles that are completely water-soluble. As granular polymers have to be dried anyway in the course of their preparation, the heat treatment step in the process according to the invention does not constitute an additional process step. Moreover, compared with the polymers known hitherto, the polymer particles prepared by the process according to the invention have an increased environmental compatibility that manifests itself especially in a lower toxicity to microorganisms, particularly algae.

The polymer particles according to the invention are particularly suitable for applications demanding a low toxicity to microorganisms. They are used preferably as flocculation aids and particularly preferably in the separation of iron in the Bayer process, in the dressing of coal and ore in mining, and in the sugar industry. They can also be used particularly preferably as flocculation aids in water processing and waste water treatment and very particularly preferably in combination with another flocculation aid in so-called dual flocculation.

The polymer particles according to the invention can also preferably be used as thickeners, as additives for water-based soil sprays or as additives for plant protection agents or erosion protection agents.

The $E_bC_{50}$ value of the agents used is preferably more than 10 mg/l.

Test Method

Determination of the Viscosity of the Polymer

The viscosity is determined on a 0.5% solution of the polymer in 10% aqueous sodium chloride solution using a Brookfield viscometer.

Determination of the Temporary Gel Content 1.0 g of the test substance is dissolved in 1 l of tap water for one hour, with stirring, and filtered through a sieve (mesh size 315 µm; diameter 200 mm; height 50 mm). The residue is washed with water and the supernatant is measured in ml.

Algae Toxicity Test

The algae toxicity is determined on *Scenedesmus subspicatus* according to OECD Guideline 201, 4th edition, "Growth Inhibition Test".

EXAMPLES

The invention is illustrated below with the aid of Examples. These illustrations are solely exemplary and do not restrict the general spirit of the invention.

The following abbreviation will be used:

ABAH 2,2'-azobis(2-methylpropionamidine) dihydrochloride

Example 1

630 g of 50% aqueous acrylamide solution, placed in a polymerization vessel, were mixed with 650 g of water and 210 mg of Versenex 80 from Dow Chemical Company. After the addition of 103.4 g of acrylic acid, the mixture was neutralized to pH 6.0 with 106 g of 50% aqueous NaOH solution and then cooled to –5° C., and nitrogen was bubbled through the solution. After the addition of 0.45 g of ABAH, the polymerization was started with UV light. The reaction mixture heated up from –5° C. to 80° C. over a polymerization time of 25 min. The polymer was then comminuted with a mincer and 300 g of this gel were mixed thoroughly with 20 g of a solution consisting of 16.1 g of water, 3.0 g of isopropanolamine and 0.9 g of ammonium sulphate, and heat-treated for 90 min at 110° C. Finally, the polymer was ground to a size fraction of 90–1400 µm.

The results of the algae toxicity test and the physical parameters of the polymer particles are listed in Table 1.

Example 2

The same monomer solution as in Example 1 was polymerized under the conditions described in said Example. The polymer was comminuted with a mincer and 300 g of this gel were mixed thoroughly with a solution consisting of 12.8 g of water, 4.5 g of isopropanolamine and 2.7 g of ammonium chloride, and heat-treated for 90 min at 110° C. Finally, the polymer was ground to a size fraction of 90–1400 µm.

The results of the algae toxicity test and the physical parameters of the polymer particles are listed in Table 1.

Comparative Example 1

The same monomer solution as in Example 1 was polymerized under the conditions described in said Example, the polymer was comminuted with a mincer and the product was then heat-treated without further additions.

The results of the algae toxicity test and the physical parameters of the polymer particles are listed in Table 1.

Comparative Example 2 (Corresponding to DE 197 52 127)

420 g of 50% aqueous acrylamide solution, placed in a polymerization vessel, were mixed with 341.2 g of water and 140 mg of Versenex 80. After the addition of 68.9 g of acrylic acid and 55.8 g of ammonium chloride, the mixture was neutralized to pH 6.0 with 70.7 g of 50% aqueous NaOH solution and then cooled to –5° C., and nitrogen was bubbled through the solution. After the addition of 0.30 g of ABAH, the polymerization was started with UV light. The reaction mixture heated up from –5° C. to 80° C. over a polymerization time of 25 min. The polymer was comminuted with a mincer and heat-treated for 90 min at 110° C. Finally, the product was ground to a size fraction of 90–1400 µm.

The results of the algae toxicity test and the physical parameters of the polymer particles are listed in Table 1.

Example 3

630 g of 50% aqueous acrylamide solution, placed in a polymerization vessel, were mixed with 579.4 g of water and 210 mg of Versenex 80. After the addition of 103.4 g of acrylic acid and 12.75 g of isopropanolamine, the mixture was neutralized to pH 6.0 with 50% aqueous NaOH solution. After neutralization, 25 g of 20% aqueous ammonium chloride solution were added and the mixture was cooled to −5° C. After nitrogen had been bubbled through, 0.45 g of ABAH was added to the mixture and the polymerization was started with UV light. The reaction mixture heated up from −5° C. to 80° C. over a polymerization time of 25 min. The polymer was comminuted with a mincer and heat-treated for 90 min at 110° C. The product was ground to a size fraction of 90–1400 μm.

The results of the algae toxicity test and the physical parameters of the polymer particles are listed in Table 1.

Example 4

The procedure was analogous to that of Example 3 except that 33 g of isopropanolamine were used instead of 12.75 g.

The results of the algae toxicity test and the physical parameters of the polymer particles are listed in Table 1.

TABLE 1

| Example | Complete solubility after 16 h | Temporary gel value (1 h) [ml] | Viscosity [mPas] | $E_bC_{50}$ value [mg/l] |
|---|---|---|---|---|
| C 1 | yes | 70 | 395 | 9 |
| C 2 | no | 180 | 100 | n.d. |
| 1 | yes | 13 | 300 | 22 |
| 2 | yes | 22 | 270 | 50 |
| 3 | yes | 19 | 250 | 22 |
| 4 | yes | 2 | 170 | >100 | n.d.—value not determined

Example 5

Polymerization was carried out as in Example 1. However, the minced gel (300 g) was then after-treated with a solution of 3.0 g of methylaminoethanol and 0.9 g of ammonium sulphate in 16.1 g of water. The subsequent work-up was carried out analogously to Example 1.

The product has a viscosity of 180 mPas and a temporary gel value (1 h) of 10 ml.

This product is also completely soluble after 16 h. The $E_bC_{50}$ value of this product is 27 mg/l.

Example 6

Polymerization was carried out as in Example 1. However, the minced gel (300 g) was then after-treated with a solution of 3.0 g of methylaminoethanol and 0.3 g of ammonium sulphate in 16.7 g of water. The subsequent work-up was carried out analogously to Example 1.

The product has a viscosity of 200 mPas and a temporary gel value (1 h) of 9 ml.

This product is also completely soluble after 16 h. The $E_bC_{50}$ value of this product is 26 mg/l.

Example 7

Polymerization was carried out as in Example 1. However, the minced gel (300 g) was then after-treated with a solution of 1.5 g of 4-amino-1-butanol and 2.7 g of ammonium sulphate in 16.8 g of water. The subsequent work-up was carried out analogously to Example 1.

The product has a viscosity of 230 mPas and a temporary gel value (1 h) of 28 ml.

This product is also completely soluble after 16 h. The $E_bC_{50}$ value of this product is 18 mg/l.

Example 8

Polymerization was carried out as in Example 1. However, the minced gel (300 g) was then after-treated with a solution of 3.0 g of 4-amino-1-butanol and 2.7 g of ammonium sulphate in 12.8 g of water. The subsequent work-up was carried out analogously to Example 1.

The product has a viscosity of 230 mPas and a temporary gel value (1 h) of 20 ml.

This product is also completely soluble after 16 h. The $E_bC_{50}$ value of this product is 18 mg/l.

Example 9

630.0 g of 50% aqueous acrylamide solution, placed in a polymerization vessel, were mixed with 579.4 g of water and 210 mg of Versenex 80. After the addition of 103.4 g of acrylic acid and 4.98 g of methylaminoethanol, the mixture was neutralized to pH 6.0 with 50% aqueous NaOH solution. After neutralization, 67.5 g of 20% aqueous ammonium sulphate solution in water were added and polymerization was carried out analogously to Example 3.

The product has a viscosity of 200 mPas and a temporary gel value (1 h) of 9 ml.

The product is completely soluble after 16 h.

The $E_bC_{50}$ value of this product is 16 mg/l.

Example 10

630.0 g of 50% aqueous acrylamide solution, placed in a polymerization vessel, were mixed with 579.4 g of water and 210 mg of Versenex 80. After the addition of 103.4 g of acrylic acid and 9.96 g of methylaminoethanol, the mixture was neutralized to pH 6.0 with 50% aqueous NaOH solution. After neutralization, 67.5 g of 20% aqueous ammonium sulphate solution in water were added and polymerization was carried out analogously to Example 3.

The product has a viscosity of 125 mPas and a temporary gel value (1 h) of 2 ml.

The product is completely soluble after 16 h.

The $E_bC_{50}$ value of this product is 19 mg/l.

What is claimed is:

1. Water-soluble polymer particles, characterized in that they have an $E_bC_{50}$ value of more than 10 mg/l in the algae toxicity test on *Scenedesmus subspicatus*.

2. Water-soluble polymer particles according to claim 1, prepared by a process comprising:
   a) polymerizing a monomer material comprising at least one (meth)acrylic acid or (meth)acrylic acid derivative;
   b) adding at least one ammonium salt and one water-soluble amine to a monomer solution prior to polymerization of the monomers in step (a), after polymerization of the monomers or at both stages; and
   c) heat-treating the polymer particles.

3. The water-soluble polymer particles according to claim 2, wherein said ammonium salt is at least one water-soluble inorganic ammonium salt or one organic ammonium salt.

4. The water-soluble polymer particles according to claim 2, wherein the concentration of said ammonium salt in the product obtained ranges from 0.05 to 10% by weight.

5. The water-soluble polymer particles according to claim 4, wherein said concentration of ammonium salt ranges from 0.2 to 3% by weight.

6. The water-soluble polymer particles according to claim 4, wherein said water-soluble amine is an alkanolamine.

7. The water-soluble polymer particles according to claim 6, wherein said alkanolamine is isopropanolamine.

8. The water-soluble polymer particles according to claim 4, wherein the concentration of amine in the product ranges from 0.1 to 12% by weight.

9. The water-soluble polymer particles according to claim 8, wherein the concentration of amine ranges from 0.5 to 5% by weight.

10. The water-soluble polymer particles according to claim 2, wherein the monomer material being polymerized further comprises
 a) at least one monoethylenically unsaturated $C_{3-10}$ monocarboxylic acid, alkali metal salt thereof, ammonium salt thereof; amine salt thereof, or combinations of said salts, and
 b) at least one other monomer copolymerizable by free radical polymerization.

11. The water-soluble polymer particles according to claim 2, wherein the polymer materials of the particles consist essentially of 1 to 99% by weight of polymerized acrylamide and 99 to 1% by weight of polymerized acrylic acid.

12. The water-soluble polymer particles according to claim 11, wherein the acrylic acid monomer in the polymer is neutralized to the extent of 1 to 100 mol%.

13. A process for the preparation of water-soluble polymer particles, comprising:
 a) polymerizing a monomer material comprising at least one (meth)acrylic acid or (meth)acrylic acid derivative;
 b) adding at least one ammonium salt and one water-soluble amine to a monomer solution prior to polymerization of the monomers in step (a), after polymerization of the monomers or at both stages; and
 c) heat-treating the polymer particles,
the water-soluble polymer particles having an $E_bC_{50}$ value of more than 10 mg/l in the algae toxicity test on *Scenedesmus subspicatus*.

14. The process according to claim 13, wherein the polymer particles are beat treated at a temperature of 80 to 120° C.

15. The process according to claim 14, wherein said temperature ranges from 90to 110° C.

16. The process according to claim 13, wherein the ammonium salt is at least one water-soluble inorganic ammonium salt, at least one organic ammonium salt, or a combination thereof.

17. The process according to claim 13, wherein said ammonium salt is added in a concentration of 0.05 to 10% by weight, based on the weight of product.

18. The process according to claim 17, wherein the concentration of ammonium salt ranges from 0.2 to 3% by weight.

19. The process according to claim 13, wherein said amine is an alkanolamine.

20. The process according to claim 19, wherein said alkanolamine is isopropanolamine.

21. The process according to claim 13, wherein the water-soluble amine is added in a concentration of 0.1 to 12% by weight, based on the weight of the product.

22. The process according to claim 21, wherein the concentration of water-soluble amine ranges from 0.5 to 5% by weight, based on the weight of the product.

23. The process according to claim 13, wherein said amine is added to the monomer solution and the ammonium salt is added to the polymer particles obtained upon polymerization before the heat treatment step.

24. The process according to claim 13, wherein the ammonium salt is added to the monomer solution before polymerization of monomers and the amine is added to the polymer particles obtained by polymerization before the heat treatment.

25. A method of processing water or treating wastewater, comprising:
 processing water or treating wastewater by adding the water-soluble polymer particles as defined in claim 1, as a flocculation aid, optionally in combination with cationic flocculation aids to the processing water or the wastewater.

26. A method of processing sugar, comprising:
 adding the water-soluble polymer particles as defined in claim 1 to aqueous sugar solutions as a flocculation aid.

27. A method of mining (ore/coal), comprising:
 in a process of mining (ore/coal), effecting the mining operation with a solution containing the water-soluble particles defined in claim 1 as a flocculation aid.

28. A method of separating iron by the Bayer process, comprising:
 in the process of separating iron from other materials in the Bayer process, employing an aqueous solution containing the water-soluble polymer particles, as defined in claim 1, as a flocculation aid.

29. A method of thickening a substance, comprising:
 incorporating the water-soluble polymer particles, as defined in claim 1, in the substance.

30. A method of protecting plants, comprising:
 treating said plants with a plant protection agent containing the water-soluble polymer particles as defined in claim 1.

31. A method of preventing soil erosion, comprising:
 treating soil with an erosion protection agent containing the water-soluble polymer particles defined in claim 1 as a constituent.

32. A method of boring holes in the ground, comprising:
 drilling bore holes in the ground employing a water-based bore hole fluid containing the water-soluble, polymer particles defined in claim 1 as a constituent.

33. Water-soluble polymer particles prepared by a process comprising:
 a) polymerizing a monomer material comprising at least one (meth)acrylic acid or (meth)acrylic acid derivative;
 b) adding at least one ammonium salt and one water-soluble amine to a monomer solution prior to polymerization of the monomers in step (a), after polymerization of the monomers or at both stages; and
 c) heat-treating the polymer particles which have an $E_bC_{50}$ value of more than 10 mg/l in the algae toxicity test on *Scenedesmus subspicatus*.

* * * * *